(12) United States Patent
Burk

(10) Patent No.: US 6,380,250 B1
(45) Date of Patent: *Apr. 30, 2002

(54) CYCLOPENTANE HEPTAN(ENE)OIC ACID, 2-THIOCARBAMOYLOXY AND 2-CARBAMOYLOXY COMPOUNDS AS THERAPEUTIC AGENTS

(75) Inventor: Robert M. Burk, Laguna Beach, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/876,808

(22) Filed: Jun. 6, 2001

Related U.S. Application Data (63) Continuation of application No. 09/671,492, filed on Sep. 27, 2000.

(51) Int. Cl.[7] ................... C07C 405/00; A01K 31/5575
(52) U.S. Cl. .......................................... 514/538; 560/33
(58) Field of Search ............................. 560/33; 514/538

(56) References Cited

U.S. PATENT DOCUMENTS

| | | |
|---|---|---|
| 4,994,274 A | 2/1991 | Chan et al. |
| 5,028,624 A | 7/1991 | Chan et al. |
| 5,034,413 A | 7/1991 | Chan et al. |
| 5,446,041 A | 8/1995 | Chan et al. |

OTHER PUBLICATIONS

Bito, L.Z., *Biological Protection with Prostaglandins*, "Prostaglandins and Related Compounds as Potential Ocular Therapeutic Agents", vol. 1, Chapter 18, 1985, pp. 231–252.
Bito, L.Z., *Glaucoma, Applied Pharmacology in the Medical Treatment*, "Prostaglandins, Other Eicosanoids, and Their Derivatives as Potential Antiglaucoma Agents",1984, Chapter 20, pp. 477–505.

Nilsson et al., Invest. Ophthalmol. Vis. Sci. (suppl), 284 (1987), Arvo Abstracts 9–6:00.

Bito, L.Z., Arch. Ophthalmol. "Prostaglandins", "Old Concepts and New Perspectives", vol. 105, pp. 1036–1039 (1987).

Siebold et al, Prodrug 5 3, "Esterified protaglandin shows 'potent' promise", 1989.

*Primary Examiner*—Robert Gerstl
(74) *Attorney, Agent, or Firm*—Robert J. Baran; Martin A. Voet; Carlos A. Fisher

(57) ABSTRACT

The invention relates to the use of cyclopentane heptan(ene) oic acid, 2-thiocarbamoyloxy and carbamoyloxy as therapeutic agents e.g. as ocular hypotensives. The compounds used in accordance with the invention are represented by the following formula I:

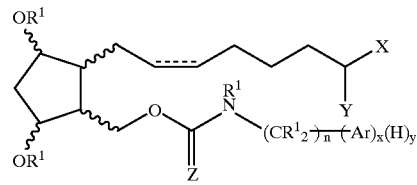

wherein a wavy segments indicate either the alpha ($\alpha$) or beta ($\beta$) configuration; the dashed bond represents a double bond or a single bond; Ar is selected from the group consisting of aryl or heteroaryl radicals having from 4 to 10 carbon atoms and substituted derivatives of said aryl and heteroaryl radicals; n is 0 or an integer of from 1 to 4; x and y are 1 or 0, provided that when x is 1, y is 0 and when x is 0, y is 1; $R^1$ is hydrogen or a lower alkyl radical or a substituted lower alkyl radical having up to six carbon atoms; X is selected from the group consisting of —$OR^1$ and —$N(R^1)_2$; Y is =O or represents 2 hydrogen radicals, and the 9 and/or 11 esters thereof and/or the pharmaceutically acceptable salts of said compounds and/or esters.

19 Claims, 3 Drawing Sheets

CYCLOPENTANE HEPTAN(ENE)OIC ACID, 2-THIOCARBAMOYLOXY AND 2-CARBAMOYLOXY COMPOUNDS AS THERAPEUTIC AGENTS

RELATED APPLICATIONS

This application is a continuation of Ser. No. 09/671,492 which was filed on Sep. 27, 2000.

BACKGROUND OF THE INVENTION

1. Field of the Invention

The present invention relates to cyclopentane heptanoic acid, 2 thiocarbamoyloxy and 2-carbamoyloxy compounds which may be substituted in the 1-position with hydroxyl, alkyloxy, amino and amido groups. These compounds are potent ocular hypotensive and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptomatic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L.Z. Biological Protection with Prostaglandins, Cohen, M.M., ed., Boca Raton, Fla., CRC Press Inc., 1985, pp. 231–252; and Bito, L.Z., Applied Pharmacology in the Medical Treatment of Glaucomas Drance, S.M. and Neufeld, A.H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., Invest. Ophthalmol. Vis. Sci. (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L.Z., Arch. Ophthalmol. 105, 1036 (1987), and Siebold et.al., Prodrug 53 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175,476 (filed Dec. 29, 1993). Similarly, 11,15- 9,15 and 9,11-diesters of prostaglandins, for example 11,15-dipivaloyl $PGF_{2\alpha}$ are known to have ocular hypotensive activity. See the patent applications U.S. Ser. No.

385,645 (filed Jul. 7, 1989, now U.S. Pat. No. 4,994,274), 584,370 (filed Sep. 18, 1990, now U.S. Pat. No. 5,028,624) and 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I wherein a wavy segment represents an α or β bond; the dashed line represents a double bond or a single bond; Z is O or S; Ar is an aryl or hetero aryl radical having from 4 to 10 carbon atoms, e.g. phenyl, furyl, thienyl, etc. or substituted aryl or a substituted heteroaryl radical; n is 0 or an integer of from 1 to 4; x and y are 1 or 0, provided that when x is 1, y is 0 and when x is 0, y is 1; $R^1$ is hydrogen or a lower alkyl radical or a substituted lower alkyl radical having up to six carbon atoms; X is selected from the group consisting of —$OR^1$ and —$N(R^1)_2$; Y is =O or represents 2 hydrogen radicals and the 9 and/or 11 esters thereof, e.g. the lower alkyl esters having up to six carbon atoms; and/or the pharmaceutically acceptable salts of said compound and/or the esters thereof. In particular, the substituents on the lower alkyl, aryl or heteroaryl radical may be selected from the group consisting of lower alkyl, e.g. C1 to C6 alkyl; hydroxy; lower alkyloxy, e.g. $OCH_3$; halogen, e.g. fluoro, chloro and bromo; trifluoromethyl ($CF_3$); $COR^1$, e.g. $COCH_3$; $COCF_3$; $SO_2NR^1$, e.g. $SO_2NH_2$; $NO_2$; CN; etc.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising
- a container adapted to dispense its contents in a metered form; and
- an ophthalmic solution therein, as hereinabove defined.

Finally, certain of the compounds represented by the above formula, disclosed below and utilized in the method of the present invention are novel and unobvious.

DETAILED DESCRIPTION OF THE INVENTION

The present invention relates to the use of cyclopentane heptan(ene)oic acid, 2-thiocarbamoyloxy and 2-carbamoyloxy as therapeutic agents, e.g. as ocular hypotensives. The compounds used in accordance with the present invention are encompassed by the following structural formula I:

wherein the substituents and symbols are as hereinabove defined. The dotted line on the bond between carbons 5 and 6 (C-5) indicates a single or double bond. If two solid lines are used at C-5, it indicates a specific configuration for that double bond.

A preferred group of the compounds of the present invention includes compounds that have the following structural formula II:

wherein n is 0 or 1, 2 or 4; hatched lines at position C-8, C-9 and C-11 indicate the α configuration; and the triangle at position C-12 represents β orientation. Preferably Y is =O.

More preferably, Ar is selected from the group consisting of phenyl, furyl and thienyl.

Another preferred group includes compounds having the formula III:

In compounds of formula III, preferably X is —$OR^1$ or $N(R^1)_2$ and Y is =O, e.g. the 1-position is a carboxylic acid or carboxylamide radical.

Preferably, $R^1$ is H.
Preferably n is 0, 1, 2 or 4.
Preferably Ar is phenyl, thienyl, chlorophenyl or trifluoromethyl phenyl.
Preferably X is OH, $NH_2$, $NHC_2H_5$ or $NHC_2H_4OH$
Preferably Y is =O.

The above compounds of the present invention may be prepared by methods that are known in the art or according to the working examples below. The compounds, below, are especially preferred representative of the compounds of the present invention.

(Z)-7-((1R,2S,3R,5S)-2-Benzylthiocarbamoyloxymethyl-3,5-dihydroxycyclopentyl)hept-5-enoic acid (Z)-7-((1R,2S,3R,5S)-2-Benzylcarbamoyloxymethyl-3,5-dihydroxycyclopentyl)hept-5-enoic acid (Z)-7-((1R,2S,3R,5S)-3,5-Dihydroxy-2-phenylcarbamoyloxymethyl-cyclopentyl)hept-5-enoic acid (Z)-7-[(1R,2S,3R,5S)-3,5-Dihydroxy-2-(2-thiophen-2-ylethycarbamoyloxymethyl)cyclopentyl]hept-5-enoic acid (Z)-7-((1R,2S,3R,5S)-2-Butylthiocarbamoyloxymethyl-3,5-dihydroxycyclopentyl)hept-5-enoic acid (Z)-7-[(1R,2S,3R,5S)-2-(3-Chlorobenzylthiocarbamoyloxymethyl)-3,5-dihydroxycyclopentyl]hept-5-enoic acid (Z)-7-[(1R,2S,3R,5S)-3,5-Dihydroxy-2-(3-trifluoromethylbenzylcarbamoyloxymethyl)cyclopentyl]hept-5-enoic acid (Z)-7-[(1R,2S,3R,5S)-3,5-Dihydroxy-2-(3-trifluoromethylbenzylthiocarbamoyloxymethyl)cyclopentyl]hept-5-enoic acid (3-Chlorobenzyl)thiocarbamic acid O-{(1S,2R,3S,5R)-3,5-dihydroxy-2-[(Z)-6-(2-hydroxyethylcarbamoyl)hex-2-enyl]cyclopentylmethyl} ester (3-Chlorobenzyl)thiocarbamic acid O-[(1S,2R,3S,5R)-2-((Z)-6-ethylcarbamoylhex-2-enyl)-3,5-dihydroxycyclopentylmethyl] ester (3-Chlorobenzyl)thiocarbamic acid O-[(1S,2R,3S,5R)-2-((Z)-6-carbamoylhex-2-enyl)-3,5-dihydroxycyclopentylmethyl] ester A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredient s are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Figure 1:
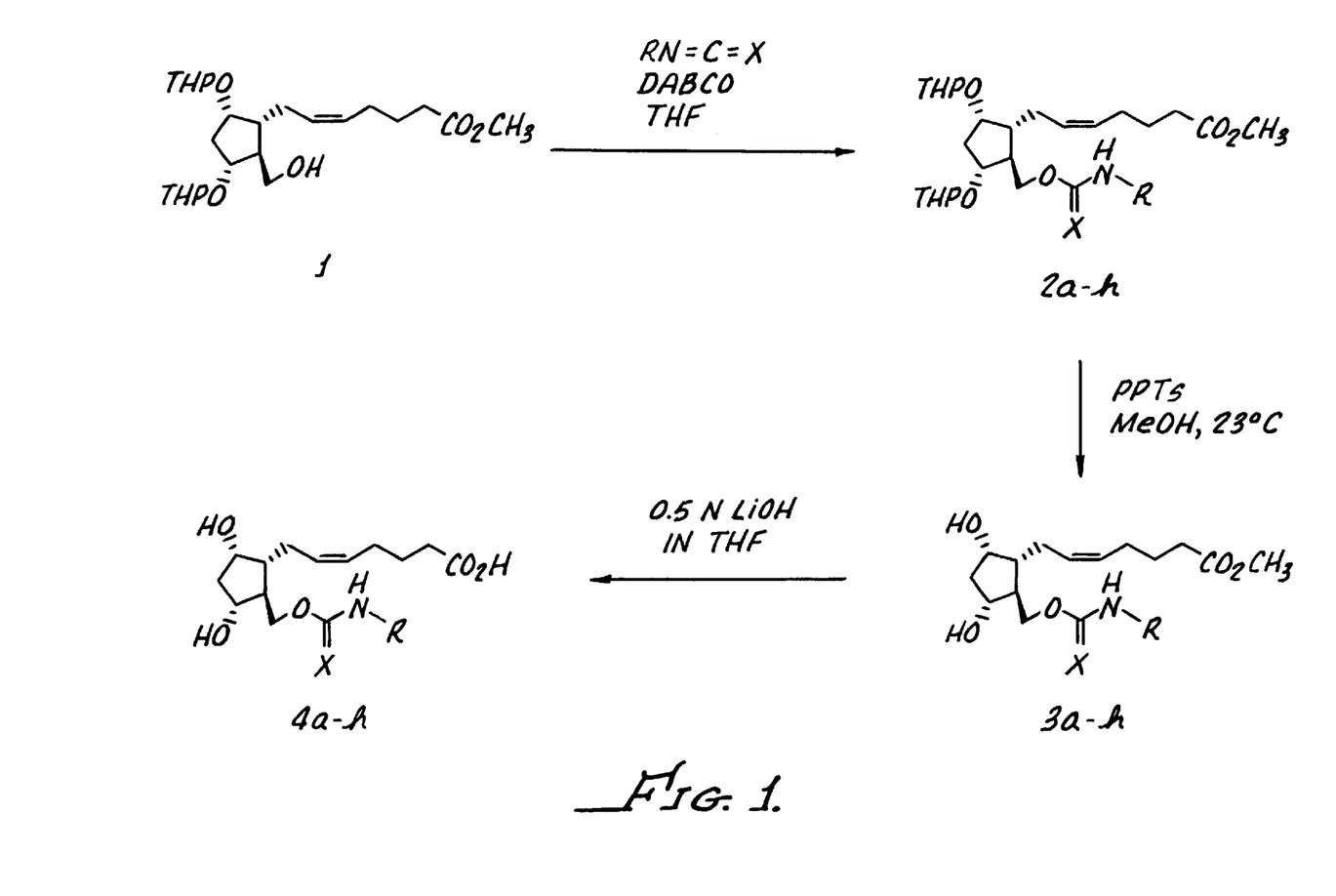
FIG. 1 is a schematic of the chemical synthesis of certain compounds of the invention, specifically disclosed as Examples 2, 3, 5, 6 and 8 through 14 below.
Figure 2:
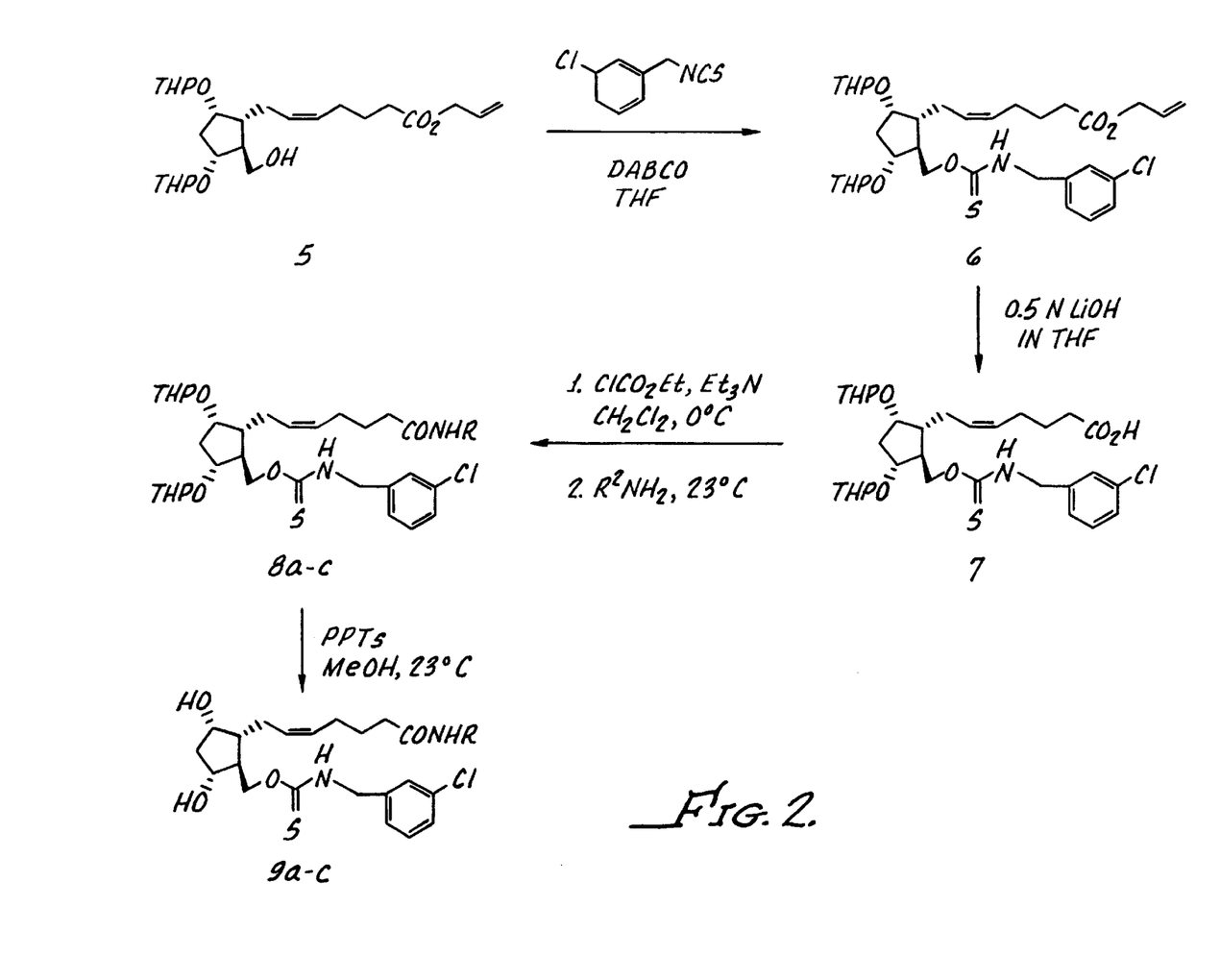
FIG. 2 is a schematic of the chemical synthesis of certain compounds of the invention, specifically disclosed as Examples 17 through 20.

The invention is further illustrated by the following non-limiting Examples, which are summarized in the reaction scheme of FIG. 1, wherein like numbers refer to the same compounds.

EXAMPLE 1

Methyl 7-[Phenylcarbamoyloxymethyl-3,5-bis(tetrahydropyran-2-yloxy)cyclopentyl]hept-5-enoate (2a).

Phenylisocyanate (68 μL, 0.63 mmol) was added to a solution of 1,4-C-diazabicyclo[2.2.2]octane (76.5 mg, 0.68 mmol) and alcohol 1 (250 mg, 0.57 mmol) in THF (3.0 mL at 23° C. After 16 h the reaction was concentrated in vacuo and the residue was purified by flash column chromatography (silica gel, 3:1 hexane/EtOAc) to afford the title compound.

EXAMPLE 2

Methyl 7-[3,5 Dihydroxy-2-phenylcarbamoyloxymethylcyclopentyl]hept-5-enoate (3a).

A solution of bis-THP ether 2a obtained above and pyridinium p-toluenesulfonate (150 mg, 0.60 mmol) in MeOH (6.0 mL) was stirred at 23° C. for 12 h. The solvent was removed in vacuo. The residue was diluted with EtOAc and washed with 1N HCl, saturated aqueous NaHCO$_3$ and brine. The organic portion was dried (MgSO$_4$), filtered and concentrated in vacuo. Flash column chromatography (silica gel, 100% EtOAc)of the residue provided 208 mg (93% over two steps) of the title compound.

EXAMPLE 3
(Z)-7-((1R,2S,3R,5S)-3,5-Dihydroxy-2-phenzylcarbamoyloxymethylcyclopentyl)-hept-5-enoic acid (4a).

A mixture of ester 3a (64 mg, 0.163 mmol) and lithium hydroxide (0.66 mL of a 0.5 N solution in H$_2$O, 0.33 mmol) in THF (1.3 mL) was stirred at 23° C. for 12 h. The reaction was acidified with 1N HCl and extracted with EtOAc. The organic portion was washed with brine (2X), dried (MgSO$_4$), filtered and concentrated in vacuo. The residue was purified by flash column chromatography (silica gel, 9:1 EtOAc/MeOH) to afford 55.3 mg (90%) of the title compound.

EXAMPLE 4
Methyl 7-[2-Benzylcarbamoyloxymethyl-3,5bis(tetrahydropyran-2-yloxy)-cyclopentyl]hept-5enoate (2b).

According to the procedures described for 2a the reaction of alcohol 1 (275 mg, 0.63 mmol), 1,4diazabicyclo[2.2.2]octane (83.6 mg, 0.75 mmol), and benzylisocyanate (99.3 mg, 0.75 mmol) afforded 182.6 mg (51%) of the title compound after purification by flash column chromatography (silica gel, 2:1 hexane/EtOAc).

EXAMPLE 5
Methyl 7-[2-Benzylcarbamoyloxymethyl-3,5dihydroxycyclopentyl]hept-5-enoate (3b).

According to the procedures described for 3a the reaction of bis-THP ether 2b (240 mg, 0.42 mmol) and pyridinium p-toluenesulfonate (100 mg, 0.40 mmol) afforded 153.1 mg (90%) of the title compound after purification by flash column chromatography (silica gel, 1:1 hexane/EtOAc).

EXAMPLE 6
7-[2-Benzylcarbamoyloxymethyl-3,5-dihydroxycyclopentyl]hept-5-enoic acid (4b).

According to the procedures described for 4a the reaction of ester 3b (40 mg, 0.99 mmol) and lithium hydroxide hydroxide (0.40 mL of a 0.5 N solution in H$_2$O, 0.20 mmol) afforded 35.6 mg (92%) of the title compound after purification by flash column chromatography (silica gel, 100% EtOAc).

EXAMPLE 7
Methyl 7-[2-Benzylthiocarbamoyloxymethyl-3,5bis(tetrahydropyran-2-yloxy)cyclopentyl]hept-5-enoate (2c).

According to the procedures described for 2a the reaction of alcohol 1 (300 mg, 0.68 mmol), 1,4-diazabicyclo[2.2.2]octane (153.0 mg, 1.36 mmol), and benzylthioisocyanate (0.14 mL, 1.02 mmol) afforded 380.3 mg (95%) of the title compound after purification by flash column chromatography (silica gel, 3:1 hexane/EtOAc).

EXAMPLE 8
Methyl 7-[2-Benzylthiocarbamoyloxymethyl-3,5-dihydroxycyclopentyl]-hept-5-enoate (3c).

According to the procedures described for 3a the reaction of bis-THP ether 2c (3 80.3 mg, 0.65 mmol) and pyridinium p-toluenesulfonate (200 mg, 0.78 mmol) afforded 246.4 mg (91%) of the title compound after purification by flash column chromatography (silica gel, 1:1 hexane/EtOAc).

EXAMPLE 9
7-[2-Benzylthiocarbamoyloxymethyl-3,5-dihydroxycyclopentyl]hept-5-enoic acid (4c).

According to the procedures described for 4a the reaction of ester 3c (60 mg, 0.142 mmol) and lithium hydroxide (0.57 mL of a 0.5 N solution in H$_2$O, 0.29 mmol) afforded 9.7 mg (17%) of the title compound after purification by flash column chromatography (silica gel, 100% EtOAc).

EXAMPLE 10
(Z)-7-[(1R,2S,3R,5S)-3,5-Dihydroxy-2-(2-thiophen-2-ylethylcarbamoyloxymethyl)cyclopentyl]hept-5-enoic acid (4d)

According to the procedures described above in Examples 1,2 and 3 for conversion of alcohol 1 to 4a, the use of (2-thiophen-2-ylethylimino)ethenone afforded 80 mg of the title compound after purification by flash column chromatography (silica gel, 100% EtOAc).

EXAMPLE 11
(Z)-7-((1R,2S,3R,5S)-2-Butylthiocarbamoyloxymethyl-3,5-dihydroxycyclopentyl)hept-5-enoic acid (4e)

According to the procedures described above in Examples 1,2 and 3 for conversion of alcohol 1 to 4a, the use of (butylimino)ethenethione in refluxing THF afforded 20 mg of the title compound after purification by flash column chromatography (silica gel, 100% EtOAc).

EXAMPLE 12
(Z)-7-[(1R,2S,3R,5S)-2-(3-Chlorobenzylthiocarbamoyloxymethyl)-3,5-dihydroxycyclopentyl]hept-5-enoic acid (4f)

According to the procedures described above in Examples 1,2 and 3 for conversion of alcohol 1 to 4a, the use of (3-chlorobenzylimino)ethenethione in refluxing THF afforded 30.5 mg of the title compound after purification by flash column chromatography (silica gel, 100% EtOAc).

EXAMPLE 13
(Z)-7-[(1R,2S,3R,5S)-3,5-Dihydroxy-2-(3-trifluoromethylbenzylcarbamoylmethyl)cyclopentyl]hept-5-enoic acid (4g)

According to the procedures described above in Examples 1,2 and 3 for conversion of alcohol 1 to 4a, the use of (3-trifluoromethylbenzylthio)ethenone afforded 20 mg of the title compound after purification by flash column chromatography (silica gel, 100% EtOAc).

EXAMPLE 14
(Z)-7-[(1R,2S,3R,5S)3,5-Dihydroxy-2-(3-trifluoromethylbenzylthiocarbamoyloxymethyl)cyclopentyl]hept-5-enoic acid (4h)

According to the procedures described above in Examples 1,2 and 3 for conversion of alcohol 1 to 4a, the use of (3-trifluoromethylbenzylthio)ethenethione in refluxing THF afforded 22.7 mg of the title compound after purification by flash column chromatography (silica gel, 100% EtOAc).

EXAMPLE 15
(Z)-7-[(1S,2R,3S,5R)-2-(3-Chlorobenzylthiocarbamoyloxymethyl)-3,5-bis-(tetrahydropyran-2-yloxy)cyclopentyl]hept-5-enoic acid allyl ester (6)

(3-Chlorobenzylimino)ethenethione (826.6 mg, 4.5 mmol) was added to a solution of alcohol 5 (717 mg, 1.54 mmol) and 1,4diazabicyclo[2.2.2]octane (345.5 mg, 3.08 mmol) in THF (10 mL) and refluxed for 24 h. The mixture was concentrated in vacuo and the residue was purified by flash column chromatography (silica gel, 2:1 hex/EtOAc) to afford 614 mg (63%) of the above titled compound.

EXAMPLE 16
(Z)-7-[(1S,2R,3S,5R)-2-(3-Chlorobenzylthiocarbamoyloxymethyl)-3,5-bis-(tetrahydropyran-2-yloxy)cyclopentyl]hept-5-enoic acid (7)

A solution of ester 6 (614 mg, 0.97 mmol) and lithium hydroxide (62 mg, 1.5 mmol) in THF/H$_2$O (1:1, 20 mL) was stirred at 23° C. for 72 h. The mixture was acidified with 1N HCl and extracted with EtOAc. The organic portion was washed with brine, dried (Na$_2$SO$_4$), filtered and concentrated in vacuo to give 430 mg of the above titled compound.

EXAMPLE 17
(3-Chlorobenzyl)thiocarbamic acid O-[(1S,2R,3S,5R)-2-[(Z)-6(2-hydroxyethylcarbamoyl)hex-2-enyl]-3,5-bis-(tetrahydropyran-2-yloxy)cyclopentylmethyl]ester (8a)

A solution of acid 7 (60 mg, 0.10 mmol) and triethylamine (30 mg, 0.30 mmol) in CH$_2$Cl$_2$ (2 mL) was cooled to 0° C. and ethylchloroformate (11 μL, 0.12 mmol) was added. After 0.5 h ethanolamine (7.2 μL, 0.12 mmol) was added and the reaction was allowed to warm to room temperature for 12 h. The reaction was diluted with EtOAc and washed with 1N HCl, saturated aqueous NaHCO$_3$ and brine. The organic portion was dried (Na$_2$SO$_4$), filtered and concentrated in vacuo. Purification of the residue by flash column chromatography (silica gel, 100% EtOAc followed by 19:1 EtOAc/MeOH) provided 40 mg of the above titled compound.

EXAMPLE 18
(3-Chlorobenzyl)thiocarbamic acid O-{(1S,2R,3S,5R)-3,5dihydroxy-2-[(Z)-6-(2-hydroxyethylcarbamoyl)hex-2-enyl]cyclopentylmethyl}ester (9a)

A solution of bis-THP ether 8a (40 mg, 0.062 mmol) and pyridinium p-toluenesulfonate (5 mg) in MeOH (1.5 mL) was stirred at 23° C. for 16 h. The solvent was removed in vacuo and the residue was diluted with EtOAc and washed with 1N HCl, saturated aqueous NaHCO$_3$ and brine. The organic portion was dried (Na$_2$SO$_4$), filtered and concentrated in vacuo. Purification of the residue by flash column chromatography (silica gel, 100% EtOAc followed by 9:1 EtOAc/MeOH) provided 20 mg of the above titled compound.

EXAMPLE 19
(3-Chlorobenzyl)thiocarbamic acid O-[(1S,2R,3S,5R)-2-((Z)6-ethylcarbamoylhex-2-enyl)-3,5-dihydroxycyclopentylmethyl] ester (9b)

According to the procedures described above in Examples 17 and 18 acid 7 was converted with use of ethylamine to 30 mg of the above titled compound.

EXAMPLE 20
(3-Chlorobenzyl)thiocarbamic acid O-[(1S,2R,3S,5R)-2-((Z)-6-carbamoylhex-2-enyl)-3,5-dihydroxycyclopentylmethyl] ester (9c)

According to the procedures described above in Examples 17 and 18 acid 7 was converted with use of ammonia to 10 mg of the above titled compound.

Certain of the above compounds were tested for activity in the various in vitro assays described below and the results are reported in Table 1, below.

TABLE 1

| AGN-# | Structure | FP/OHL | FP$_{vasc}$ | FP/FPvasc Ratio | TP$_{vasc}$ |
|---|---|---|---|---|---|
| 3 | HO, ... CO$_2$H ... HO ... O-C(=O)-NH-phenyl | >10$^4$ | 19300 | >0.05 | |
| 6 | HO, ... CO$_2$H ... HO ... O-C(=O)-NH-CH$_2$-phenyl | 4470 | 14177 | 0.3 | |
| 9 | HO, ... CO$_2$H ... HO ... O-C(=S)-NH-CH$_2$-phenyl | 43 | 427 | 0.1 | >>10$^4$ |

TABLE 1-continued

| AGN-# | Structure | FP/OHL | FP$_{vasc}$ | FP/FPvasc Ratio | TP$_{vasc}$ |
|---|---|---|---|---|---|
| 10 | | 4571 | 31,954 | 0.14 | |
| 11 | | 130 | 171 | 0.8 | |
| 12 | | 1.5 | 3 | 0.5 | NA |
| 13 | | 1008 | 2835 | 0.4 | |
| 14 | | 16 | 178 | 0.09 | NA |
| 18 | | 24 | 11000 | 0.002 | |
| 19 | | 36 | 2912 | 0.01 | NA |

TABLE 1-continued

| AGN-# | Structure | FP/ OHL | $FP_{vasc}$ | FP/FPvasc Ratio | $TP_{vasc}$ |
|---|---|---|---|---|---|
| 20 | [structure] | 4.6 | 274 | 0.02 | |

Activity at different prostanoid receptors was measured in vitro in isolated smooth muscle preparations. FP-activity was measured as contraction of the isolated feline iris sphincter. Activity was also measured as relaxation of smooth muscle of isolated rabbit jugular vein a preparation which appears to contain a unique $PGF_{2\alpha}$-sensitive receptor provisionally termed $FP_{VASC}$. TP-vasoconstrictor activity was measured as contraction of rings of the isolated rat thoracic aorta.

Other potential therapeutic applications are in osteoporosis, constipation, renal disorders, sexual dysfunction, baldness, diabetes, cancer and in disorder of immune regulation.

Many examples also have pronounced activity at the FP receptor, provisionally termed FP associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

Figure 3:
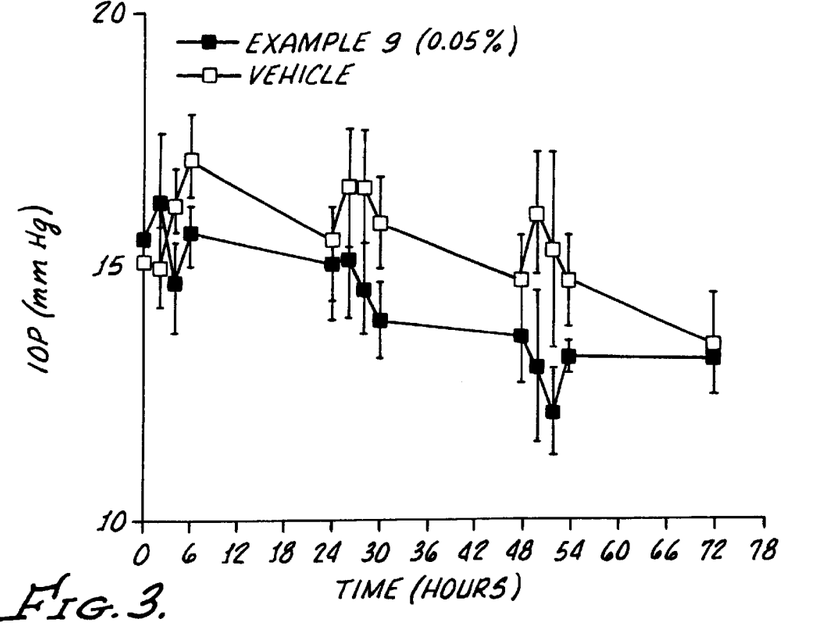
FIG. 3 shows the IOP-lowering effect of the compound of Example 9.
Figure 4:
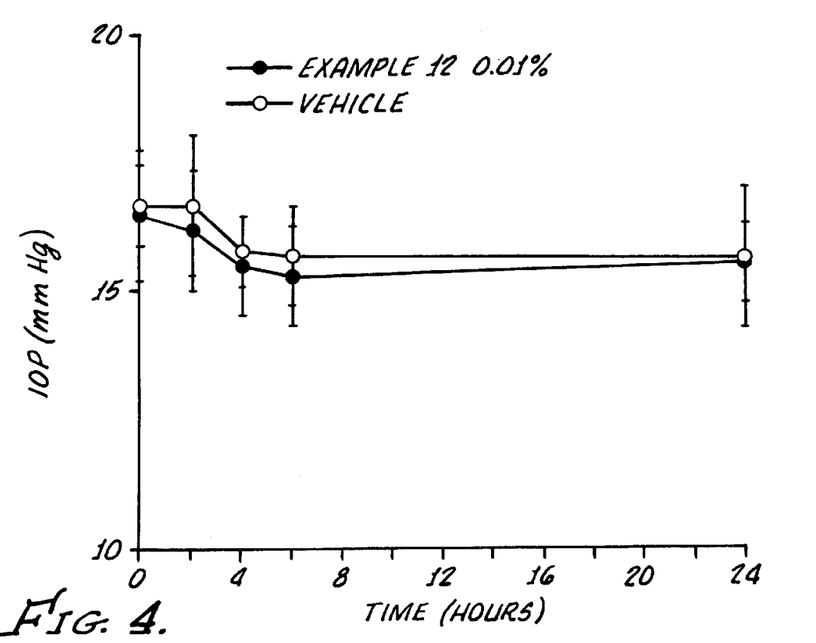
FIG. 4 shows the IOP-lowering effect of the compound of Example 12.

The effects of the compounds of this invention on intraocular pressure are also provided in FIGS. 3 and 4. The compounds were prepared at the said concentrations in a vehicle comprising 0.1% polysorbate 80 and 10 mM TRIS base. Dogs were treated by administering 25 μl to the ocular surface, the contralateral eye received vehicle as a control. Intraocular pressure was measured by applanation pneumatonometry. Dog intraocular pressure was measured immediately before drug administration and at 6 hours thereafter. The compounds of Examples 9 and 12 both lowered intraocular pressure.

The compounds of the invention may also be useful in the treatment of various pathophysiological diseases including acute myocardial infarction, vascular thrombosis, hypertension, pulmonary hypertension, ischemic heart disease, congestive heat failure, and angina pectoris, in which case the compounds may be administered by any means that effect vasodilation and thereby relieve the symptoms of the disease. For example, administration may be by oral, transdermal, parenterial, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petroatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable. For administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally containing gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension which comprises administering to a mammal having ocular hypertension a therapeutically effective amount of a compound represented by formula I:

wherein a wavy segments indicate either the alpha (α) or beta (β) configuration; the dashed bond represents a double bond or a single bond; Ar is a heteroaryl radical selected from the group consisting of thienyl and furyl radicals and substituted derivatives thereof; n is 0 or an integer of from 1 to 4; x is 1 and y is 0; $R^1$ is hydrogen or a lower alkyl radical or a substituted lower alkyl radical having up to six carbon atoms wherein the substituent on the lower alkyl or heteroaryl radical is selected from the group consisting of lower alkyl, hydroxy, lower alkyloxy, halogen, trifluoromethyl ($CF_3$), $COR_1$, $COCF_3$, $SO_2NR_1$, $SO_2NH_2$, $NO_2$ and CN.; X is selected from the group consisting of —$OR^1$ and —$N(R^1)_2$; Y is =O or represents 2 hydrogen radicals, and the 9 and/or 11 esters thereof and/or the pharmaceutically acceptable salts of said compounds and/or esters.

2. The method of claim 1 wherein said compound is represented by formula II:

wherein n is 0 or 1, 2 or 4; hatched lines at position C-8, C-9 and C-11 indicate the α orientation; and the triangle at position C-12 represents the β orientation.

3. The method of claim 2 wherein when Y is =O.

4. The method of claim 3 wherein said compound is represented by formula III:

5. The method of claim 4 wherein X is —OH, $NH_2$, $NHC_2H_5$ or $NHC_2H_4OH$.

6. The method of claim 5 wherein Y is =O and X is —OH.

7. The method of claim 5 wherein Y is =O and X is —$NH_2$, $NHC_2H_5$ or $NHC_2H_4OH$.

8. The method of claim 6 wherein said compound is:
Z)-7-[(1R,2S,3R,5S)-3,5-Dihydroxy-2-(2-thiophen-2-ylethylcarbamoyloxymethyl)cyclopentyl]hept-5enoic acid.

9. An ophthalmic solution comprising a therapeutically effective amount of a compound of formula I:

wherein a wavy segments indicate either the alpha (α) or beta (β) configuration; the dashed bond represents a double bond or a single bond; Ar is selected from the group consisting of aryl or heteroaryl radicals having from 4 to 10 carbon atoms and substituted derivatives of said aryl and heteroaryl radicals; n is 0 or an integer of from 1 to 4; x and y are 1 or 0, provided that when x is 1, y is 0 and when x is 0, y is 1; $R^1$ is hydrogen or a lower alkyl radical or a substituted lower alkyl radical having up to six carbon atoms; X is selected from the group consisting of —$OR^1$ and —$N(R^1)_2$; Y is =O or represents 2 hydrogen radicals, and the 9 and/or 11 esters thereof and/or the pharmaceutically acceptable salts of said compounds and/or esters, or a pharmaceutically acceptable salt thereof, in admixture with a non-toxic, ophthalmically acceptable liquid vehicle, packaged in a container suitable for metered application.

10. The ophthalmic solution of claim 9 wherein said compound is a compound of Formula III:

wherein n is 0 or 1, 2 or 4; hatched lines at position C-8, C-9 and C-11 indicate the α orientation; and the triangle at position C-12 represents the β orientation.

11. A pharmaceutical product, comprising a container adapted to dispense the contents of said container in metered form; and an ophthalmic solution in said container comprising a compound of formula I:

wherein a wavy segments indicate either the alpha (α) or beta (β) configuration; the dashed bond represents a double bond or a single bond; Ar is selected from the group consisting of aryl or heteroaryl radicals having from 4 to 10 carbon atoms and substituted derivatives of said aryl and heteroaryl radicals; n is 0 or an integer of from 1 to 4; x and y are 1 or 0, provided that when x is 1, y is 0 and when x is 0, y is 1; $R^1$ is hydrogen or a lower alkyl radical or a substituted lower alkyl radical having up to six carbon atoms; X is selected from the group consisting of —$OR^1$ and —$N(R^1)_2$; Y is =O or represents 2 hydrogen radicals, and the 9 and/or 11 esters thereof and/or the pharmaceutically acceptable salts of said compounds and/or esters, or a pharmaceutically acceptable salt thereof, in admixture with a non-toxic, ophthalmically acceptable liquid vehicle.

12. The product of claim 11 wherein said compound is a compound of Formula III:

wherein n is 0 or 1, 2 or 4; hatched lines at position C-8, C-9 and C-11 indicate the α orientation; and the triangle at position C-12 represents the α orientation.

13. The compound represented by Formula I:

wherein a wavy segments indicate either the alpha (α) or beta (β) configuration; the dashed bond represents a double bond or a single bond; Ar is a heteroaryl radical selected from the group consisting of thienyl and furyl radicals and substituted derivatives thereof; n is 0 or an integer of from 1 to 4; x is 1 and y is 0; $R^1$ is hydrogen or a lower alkyl radical or a substituted lower alkyl radical having up to six carbon atoms wherein the substituent on the lower alkyl or heteroaryl radical is selected from the group consisting of lower alkyl, hydroxy, lower alkyloxy, halogen, trifluoromethyl ($CF_3$), $COR_1$, $COCF_3$, $SO_2NR_1$, $SO_2NH_2$, $NO_2$ and CN.; X is selected from the group consisting of —$OR^1$ and —$N(R^1)_2$; Y is =O or represents 2 hydrogen radicals, and the 9 and/or 11 esters thereof and/or the pharmaceutically acceptable salts of said compounds and/or esters.

14. The compound of claim 13 wherein said compound is formula II wherein n is 0 or 1, 2 or 4; hatched lines at position C-8, C-9 and C-11 indicate the α orientation; and the triangle at position C-12 represents the β orientation.

15. The compound of claim 14 wherein said compound is formula III:

16. The compound of claim 15 wherein X is —OH, —$NH_2$, $NHC_2H_5$ or $NHC_2H_4OH$.

17. The compound of claim 16 wherein Y is =O and X is —OH.

18. The compound of claim 16 wherein Y is =O and X is —$NH_2$, $NHC_2H_5$ or $NHC_2H_4OH$.

19. The compound of claim 18 wherein said compound is:

Z)-7-[(1R,2S,3R,5S)-3,5-Dihydroxy-2-(2-thiophen-2-ylethylcarbamoyloxymethyl)cyclopentyl]hept-5-enoic acid.

* * * * *

UNITED STATES PATENT AND TRADEMARK OFFICE
CERTIFICATE OF CORRECTION

PATENT NO. : 6,380,250 B1
DATED : April 30, 2002
INVENTOR(S) : Burk et al.

It is certified that error appears in the above-identified patent and that said Letters Patent is hereby corrected as shown below:

Column 3,
Line 37, delete "C1 to C6" and insert in place thereof -- $C_1$-$C_6$ --

Column 6,
Line 22, delete "ingredient s" and insert in place thereof -- ingredients --
Line 56, after "1,4-" delete "C"

Column 7,
Line 26, delete "1-4diazabicyclo" and insert in place thereof -- 1-4-diazacyclo --
Line 34, delete "3,5dihydroxycyclopentyl" and insert in place thereof -- 3,5-dihydroxycyclopentyl --
Line 51, delete "5bis" and insert in place thereof -- 5-bis --

Column 8,
Line 44, delete "3-trifluoromethylbenzylthio" and insert in place thereof -- trifluoromethylbenzylimino --
Line 65, delete "1,4diazabicyclo" and insert in place thereof -- 1,4-diazabicyclo --

Column 9,
Line 32, delete "3,5dihydroxy" and insert in place thereof -- 3,5-dihydroxy --

Column 12,
AGN #18, under heading Tpvasc, insert -- NA --

Column 16,
Line 22, delete "5enoic" and insert in place thereof -- 5-enoic --

Column 17,
Line 40, delete "$\alpha$" and insert in place thereof -- $\beta$ --

Signed and Sealed this

Twenty-third Day of July, 2002

*Attest:*

JAMES E. ROGAN
*Attesting Officer*    *Director of the United States Patent and Trademark Office*